United States Patent
DePristo et al.

(10) Patent No.: US 11,335,438 B1
(45) Date of Patent: May 17, 2022

(54) DETECTING FALSE POSITIVE VARIANT CALLS IN NEXT-GENERATION SEQUENCING

(71) Applicant: Verily Life Sciences LLC, Mountain View, CA (US)

(72) Inventors: Mark Andrew DePristo, Palo Alto, CA (US); Ryan Poplin, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 985 days.

(21) Appl. No.: 15/490,572

(22) Filed: Apr. 18, 2017

Related U.S. Application Data

(60) Provisional application No. 62/333,130, filed on May 6, 2016.

(51) Int. Cl.
| | | |
|---|---|---|
| *G01N 33/48* | (2006.01) | |
| *G01N 33/50* | (2006.01) | |
| *G16B 40/00* | (2019.01) | |
| *G06N 3/08* | (2006.01) | |
| *G06N 3/04* | (2006.01) | |
| *G06N 7/00* | (2006.01) | |

(52) U.S. Cl.
CPC .............. *G16B 40/00* (2019.02); *G06N 3/04* (2013.01); *G06N 3/088* (2013.01); *G06N 7/005* (2013.01)

(58) Field of Classification Search
CPC ......... G06F 19/22; G06F 19/18; G16B 40/00; G06N 7/005; G06N 3/04; G06N 3/088
See application file for complete search history.

(56) References Cited

U.S. PATENT DOCUMENTS

| | | | | | |
|---|---|---|---|---|---|
| 5,674,743 | A | * | 10/1997 | Ulmer | ................. B01J 19/0046 435/287.2 |
| 5,845,049 | A | * | 12/1998 | Wu | ....................... G16B 40/00 706/20 |
| 2007/0134233 | A1 | * | 6/2007 | Seng | ..................... C07K 16/00 424/133.1 |
| 2010/0092959 | A1 | * | 4/2010 | Dorak | ................. C12Q 1/6886 435/6.12 |
| 2013/0073214 | A1 | * | 3/2013 | Hyland | ................. G16B 30/00 702/19 |
| 2013/0245958 | A1 | * | 9/2013 | Forster | .................. G16B 30/00 702/19 |
| 2014/0371109 | A1 | * | 12/2014 | McMillen | .......... G06F 13/4068 506/38 |
| 2016/0071005 | A1 | * | 3/2016 | Wang | ..................... G06F 17/15 706/25 |

OTHER PUBLICATIONS

'A Novel Neural Network Technique for Analysis and Classification of EM Single-Particle Images', 2001, Pascula-Montano, Journal of Structural Biology 133, 233-245 (2001).*

Craig et al. Ordering of cosmid clones covering the Herpes simplex virus type I (HSV-I) genome: a test case for fingerprinting by hybridisation. Nucleic Acids Research, vol. 18, pp. 2653-2660. (Year: 1990).*

Zhu et al. A massively parallel computational method of reading index files for SOAPsnv. Interdiscip Sci Comput Life Sci. vol. 7, pp. 397-404. (Year: 2015)*

\* cited by examiner

*Primary Examiner* — Russell S Negin
(74) *Attorney, Agent, or Firm* — McDonnell Boehnen Hulbert & Berghoff LLP

(57) ABSTRACT

A method for detecting false positive variant calls in a next generation sequencing analysis pipeline involves obtaining a plurality of read pileup windows associated with a first sample genome. The method also involves obtaining, for each reference nucleotide position represented in the plurality of read pileup windows, a label indicating that the reference nucleotide position is either (i) a known variant or (ii) a non-variant. The method further involves training a neural network based on data indicative of the plurality of read pileup windows and the labels. Additionally, the method involves receiving a read pileup window associated with a second sample genome. Further, the method involves determining, using the trained neural network, a likelihood that the read pileup window associated with the second sample genome represents a variant.

20 Claims, 12 Drawing Sheets

| Variant Call | Likelihood of False Positive |
|---|---|
| Variant 1 | 0.9 |
| Variant 2 | 0.1 |
| Variant 3 | 0.7 |
| . . . | . . . |

600

DETECTING FALSE POSITIVE VARIANT CALLS IN NEXT-GENERATION SEQUENCING

CROSS-REFERENCE TO RELATED APPLICATION

This application claims the benefit of and incorporates by reference the content of U.S. Provisional App. No. 62/333,130, filed May 6, 2016.

BACKGROUND

Early DNA sequencing techniques, such as chain-termination methods, provided reliable solutions for reading individual DNA fragments. See Sanger, F. et. al. (1977) DNA sequencing with chain-terminating inhibitors. Proc. Natl. Acad. Sci. U.S.A. 74, 5463-5467. While these first-generation technologies are effective for sequencing target genes, applying them to sequencing entire chromosomes or genomes is costly and expensive. For example, the first sequencing of a human genome—which was accomplished using the Sanger method—cost hundreds of millions of dollars and took over a decade to complete. This high cost was largely due to the sequential nature of first-generation sequencing methods; each fragment had to be individually read and manually assembled to construct a full genome.

Next generation sequencing (NGS) technologies have significantly reduced the cost of DNA sequencing by par-allelizing DNA fragment reading. Some NGS methods are capable of performing millions of sequence reads concurrently, generating data for millions of base pairs in a matter of hours. See Hall, N. (2007) Advanced sequencing technologies and their wider impact in microbiology. The Journal of Experimental Biology, 209, 1518-1525. Many NGS technologies have been proposed, and employ various chemical processes, use varying read lengths, and have demonstrated various ranges of accuracy. See Metzker, M. (2010) Sequencing technologies—the next generation. Nature Reviews, Genetics, Volume 11, 31-46; see also Shendure, J. et. al. (2008) Next-generation DNA sequencing. Nature Reviews, Biotechnology, Volume 26, Number 10, 1135-1145.

NGS methods generally involve separating a DNA sample into fragments and reading the nucleotide sequence of those fragments in parallel. The resulting data generated from this process includes read data for each of those fragments, which contains a continuous sequence of nucleotide base pairs (G, A, T, C). However, while the arrangement of base pairs within a given fragment read is known, the arrangement of the fragment reads with respect to each other is not. Thus, to determine the sequence of a larger DNA strand (such as a gene or chromosome), read data from multiple fragments must be aligned. This alignment is relative to other read fragments, and may include overlapping fragments, depending upon the particular NGS method used. Some NGS methods use computational techniques and software tools to carry out read data alignment.

Once the read data has been aligned, that aligned data may be analyzed to determine the nucleotide sequence for a gene locus, gene, or an entire chromosome. However, differences in nucleotide values among overlapping read fragments may be indicative of a variant, such as a single-nucleotide polymorphism (SNP) or an insertion or deletion (INDELs), among other possible variants. For example, if read fragments that overlap at a particular locus differ, those differences might be indicative of a heterozygous SNP. As another example, if overlapping read fragments are the same at a single nucleotide, but differ from a reference genome, that gene locus or gene may be a homozygous SNP with respect to that reference genome. Accurate determination of such variants is an important aspect of genome sequencing, since those variants could represent mutations, genes that cause particular diseases, and/or otherwise serve to genotype a particular DNA sample.

The demand for high efficiency and low-cost DNA sequencing has increased in recent years. Although NGS technologies have dramatically improved upon first-generation technologies, the highly-parallelized nature of NGS techniques has presented challenges not encountered in earlier sequencing technologies. Errors in the read process can adversely impact the alignment of the resulting read data, and can subsequently lead to inaccurate sequence determinations. Furthermore, read errors can lead to erroneous detection of variants.

A more comprehensive and accurate understanding of both the human genome as a whole and the genomes of individuals will improve medical diagnoses and treatment. NGS technologies have reduced the time and cost of sequencing an individual's genome, which provides the potential for significant improvements to medicine and genetics in ways that were previously not feasible. Understanding genetic variation among humans provides a framework for understanding genetic disorders and Mendelian diseases. However, discovering these genetic variations depends upon reliable read data.

SUMMARY

The present disclosure generally relates to detecting false positive variant calls in next generation sequencing data analysis. In one example, a method is disclosed. The method involves obtaining a plurality of read pileup windows associated with a first sample genome. Each read pileup window includes a plurality of sequence reads that each include a nucleotide aligned at a reference nucleotide position within the first sample genome. The method also involves obtaining, for each reference nucleotide position represented in the plurality of read pileup windows, a label indicating that the reference nucleotide position is either (i) a known variant or (ii) a non-variant. The method further involves training a neural network based on data indicative of the plurality of read pileup windows and the labels. Additionally, the method involves receiving a read pileup window associated with a second sample genome. Further, the method involves determining, using the trained neural network, a likelihood that the read pileup window associated with the second sample genome represents a variant.

In another example, a non-transitory computer-readable medium is disclosed. The non-transitory computer-readable medium has instructions stored thereon that, upon execution by at least one processor, causes performance of a set of operations. The operations include obtaining a plurality of read pileup windows associated with a first sample genome. Each read pileup window includes a plurality of sequence reads that each include a nucleotide aligned at a reference nucleotide position within the first sample genome. The operations also include obtaining, for each reference nucleotide position represented in the plurality of read pileup windows, a label indicating that the reference nucleotide position is either (i) a known variant or (ii) a non-variant. The operations further include training a neural network based on data indicative of the plurality of read pileup windows and the labels. Additionally, the operations include receiving a read pileup window associated with a second sample genome. Further, the operations include determining, using the trained neural network, a likelihood that the read pileup window associated with the second sample genome represents a variant.

In still another example, a method is disclosed. The method involves receiving a read pileup window associated with a second sample genome. The read pileup window includes sequence reads generated using a particular read process. The method also involves obtaining, from a model library, a trained model associated with the particular read process. The model library includes a plurality of trained models associated with a respective plurality of read processes. The method further involves determining, using the trained model, a likelihood that the read pileup window associated with the second sample genome represents a variant. Additionally, the method involves providing the likelihood as an output signal to a computing device.

In yet another example, a system is disclosed. The system includes a means for obtaining a plurality of read pileup windows associated with a first sample genome. Each read pileup window includes a plurality of sequence reads that each include a nucleotide aligned at a reference nucleotide position within the first sample genome. The system also includes a means for obtaining, for each reference nucleotide position represented in the plurality of read pileup windows, a label indicating that the reference nucleotide position is either (i) a known variant or (ii) a non-variant. The system further includes a means for training a neural network based on data indicative of the plurality of read pileup windows and the labels. Additionally, the system includes a means for receiving a read pileup window associated with a second sample genome. Further, the system includes a means for determining, using the trained neural network, a likelihood that the read pileup window associated with the second sample genome represents a variant.

The foregoing summary is illustrative only and is not intended to be in any way limiting. In addition to the illustrative aspects, embodiments, and features described above, further aspects, embodiments, and features will become apparent by reference to the figures and the following detailed description and the accompanying drawings.

DETAILED DESCRIPTION

Figure 1:
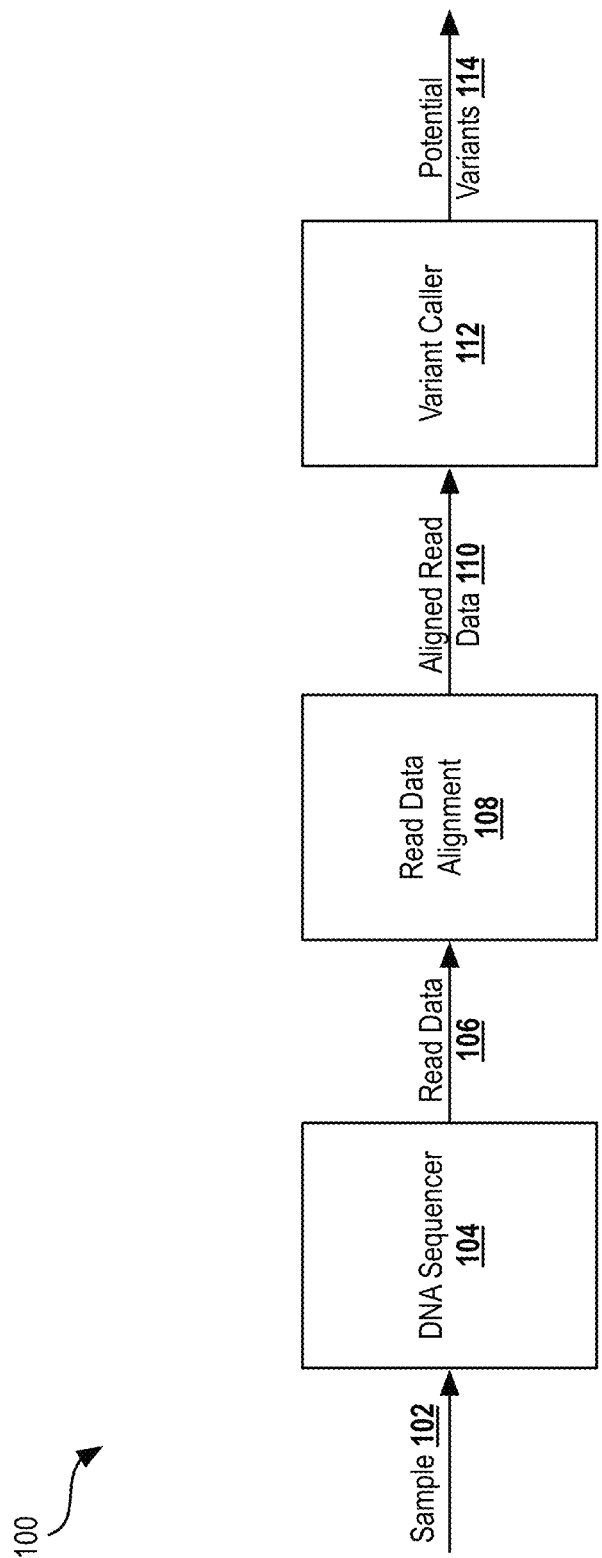
FIG. 1 illustrates a block diagram of a DNA sequencing pipeline, according to an example embodiment.

The following detailed description describes various features and functions of the disclosed systems and methods with reference to the accompanying figures. The illustrative system and method embodiments described herein are not meant to be limiting. It may be readily understood that certain aspects of the disclosed systems and methods can be arranged and combined in a wide variety of different configurations, all of which are contemplated herein.

I. INTRODUCTION

Next generation sequencing (NGS) has dramatically reduced the time and cost required to sequence an entire genome. Previous techniques involved sequentially reading out DNA fragments and having trained biochemists arrange the read data to determine the sequence of entire chromosomes. NGS technologies substantially parallelize the sequencing process, allowing millions of DNA fragments to be read simultaneously. Automated computational analyses then attempt to align the read data to determine the nucleotide sequence of a gene locus, gene, chromosome, or entire genome.

The increasing prevalence of NGS technologies have generated a substantial amount of genome data. Analysis of this genome data—both for an individual sample and for multiple samples—can provide meaningful insights about the genetics of a sample or species. Variations between genomes may correspond to different traits or diseases within a species. Variations may take the form of single nucleotide polymorphisms (SNPs), insertions and deletions (INDELs), and structural differences in the DNA itself such as copy number variants (CNVs) and chromosomal rearrangements. By studying these variations, scientists and researchers can better understand differences within a species, the causes of certain diseases, and can provide better clinical diagnoses and personalized medicine for patients.

The quality and accuracy of genome datasets is crucial to all subsequent analyses and research performed on those datasets. However, NGS technologies used to generate these genome datasets are imperfect, and sources of error in both the read process itself and the read data alignment can lead to uncertainty. If an NGS machine incorrectly reads a nucleobase and records it in the read data, subsequent analysis could incorrectly identify a variant at that locus. If there are inaccuracies in the alignment of the read data, incorrect variant detection might also occur. If these sources of error are left unaccounted for, false positive variant detection could lead to incorrect clinical diagnoses or the discovery of non-existent variants.

To mitigate these errors, some NGS analysis pipelines include filtering steps to detect and discard of false positive variant detections. Herein, a variant detection may be referred to as a "variant call." Some filtering techniques utilize hard filters that analyze one or more aspects of a variant call, compare it against one or more criteria, and provide a binary decision as to whether it is a true positive variant call or a false positive variant call. For example, if multiple read fragments aligned at a particular locus show three or more different bases, a hard filter might determine that the variant call is a false positive.

Other filtering techniques employ statistical or probabilistic models, and may involve performing statistical inferences based on one or more hand-selected variables of the variant call. A variant call might include a set of read data of DNA fragments aligned with respect to each other. Each DNA fragment read data may include metadata that specifies a confidence level of the accuracy of the read (i.e., the quality of the bases), information about the process used to read the DNA fragments, and other information. DNA sequencing experts may choose features of a variant call that they believe to differentiate true positives from false positives. Then, a statistical model (e.g., a Bayesian mixture model) may be trained using a set of labeled examples (e.g., known true variant calls and the quantitative values of the hand-selected features). Once trained, new variant calls may be provided to the statistical model, which can determine a confidence level indicative of how likely the variant call is a false positive.

One approach involving such statistical model filtering involves a set of five steps: (1) initial read alignment; (2) local realignment around INDELs; (3) base quality score recalibration; (4) SNP discovery and genotyping to find all potential variants; and (5) applying the statistical model to separate true variants from false variants produced by machine artifacts. See Depristo, M. A. et al. (2001) A framework for variation discovery and genotyping using next-generation DNA sequencing data. Nat. Genet. 43, 491-498.

The effectiveness of false positive filtering using statistical models is limited by features chosen by the designer of an NGS analysis pipeline. This deficiency is likely a result of an inadequate representation of the true sources of variation by the handcrafted features. However, the features that distinguish true positive from false positives, and the relative importance of each of those features, is generally not known prior to training. Thus, improving the accuracy of such a statistical model may involve manually assessing this filtering, examining the outputs, and selecting different features and/or tuning the weighting of each of these features in the statistical analysis. In some circumstances, a variant call may include dozens or hundreds of read fragments (of varying lengths), each of which could include dozens or hundreds of nucleotides. Thus, the number of permutations of a variant call is incredibly large. Accordingly, it would be impractical or nearly impossible for a human to analyze the effectiveness of each possible feature of a variant call.

Analysis pipelines, techniques, and methods disclosed herein involve using deep learning to autonomously extract features from variant call data, and training a model to detect false positives based on these autonomously extracted features. Unlabeled variant calls based on read data of a reference genome may first be used to perform unsupervised training of a model—such as a convolutional neural network (CNN)—to generate a background model. This background model may automatically identify features that distinguish variant calls from each other. The background model and labeled variant calls of the reference genome may then be used to perform supervised learning of a classifier. Once trained, the classifier may then applied to variant calls based on read data from a different genome (generating using the same read process as the reference genome) to determine the likelihood of each variant call being a false positive.

Many different read processes may be used to generate DNA fragment read data of a sample. Each read process may vary by read length, amplification method, materials used, and the technique used (e.g., chain termination, ligation, etc.). The nature and source of the errors of each read process may vary. Thus, the features that distinguish false positive variant calls and true positive variant calls may differ among read processes. Accordingly, the above-described technique may be applied to multiple different read processes to develop a library of classifiers. In this manner, an NGS analysis pipeline may be capable of accurately detecting false positive variant calls from read data generated by a variety of read processes.

A classifier trained in the manner described above may receive as input a set of variant calls, and may subsequently output a set of probabilities or confidence values corresponding to those variant calls. Each probability or confidence value may indicate the likelihood that a particular variant call is a false positive. Subsequent analyses may be carried out based on these probability or confidence value outputs. As one example, all variant calls whose corresponding confidence value is greater than 0.9 may be identified as a false positive. As another example, the confidence values may be used to make qualitative determinations to inform clinical diagnoses or other genetic assessments for an individual. As yet another example, confidence value data associated with a reference genome may provide a basis for identifying the sources of error in a particular NGS sequencer, mistakes in the operation of a particular NGS sequencer, bugs or errors in the alignment of read data, and/or any other source of error. An output or report of these errors may be used by NGS sequencer vendors or genetic data analysis toolkit developers to mitigate or eliminate those sources of error.

As the proliferation of NGS technologies continues, the amount of available NGS read data will increase. An existing background model may be trained using new data as it becomes available, improving the robustness of that background model. Likewise, as more sample genomes are studied become gold standard reference genomes, labeled variant calls from those new reference genomes may be used to improve the robustness and accuracy of existing classifiers. Thus, an NGS analysis pipeline with background models and classifiers described herein may improve as more training data becomes available.

II. TERMINOLOGY

A. Next Generation Sequencing (NGS)

NGS generally refers to DNA sequencing techniques that involve sequencing multiple DNA fragments of a sample in parallel. The output data may contain nucleotide sequences for each read, which may then be assembled to form longer sequences within a gene, an entire gene, a chromosome, or a whole genome. The specific aspects of a particular NGS technique may vary depending on the sequencing instrument, vendor, and a variety of other factors. Secondary analyses may then involve detecting variants within that sample.

FIG. 1 illustrates a block diagram of a DNA sequencing pipeline 100, according to an example embodiment. The pipeline 100 includes DNA sequencer 104, read data alignment 108, and variant caller 112. As described herein, a "pipeline" may refer to a combination of hardware and/or software that receives an input material or data and generates a model or output data. Pipeline 100 receives a DNA sample 102 as input, which is sequenced by the DNA sequencer 104 and outputs read data 106. The read data alignment 108 then receives the raw input read data 106 and generates aligned read data 110. The variant caller 112 analyzes the aligned read data 110 and outputs potential variants 114.

Sample 102 may be a biological sample (e.g., biopsy material) taken from a particular organism (e.g., a human). The sample 102 may be isolated DNA or RNA, and may contain individual genes, gene clusters, full chromosomes, or entire genomes. The sample 102 may include material or DNA isolated from two or more types of cells within a particular organism.

DNA sequencer 104 may be any scientific instrument that performs DNA sequencing autonomously or semi-autonomously. The DNA sequencer 104 may receive sample 102 as an input, carry out steps to break down an analyze the sample 102, and generate read data 106 containing nucleotide sequences of read fragments. The DNA sequencer 104 may subject DNA from sample 102 to fragmentation and/or ligation to produce a set of DNA fragments. The fragments may then be amplified (e.g., using polymerase chain reaction (PCR)) to produce copies of each DNA fragment. Then, the DNA sequencer 104 may sequence the amplified DNA fragments using, for example, imaging techniques that illuminate the fragments and measure the light reflecting off them to determine the nucleotide sequence of the fragments. Those nucleotide sequence reads may then be output as read data 106 (e.g., a text file with the nucleotide sequence and other metadata) and stored onto a storage medium.

Read data alignment 108 may be any combination of hardware and software that receives raw DNA fragment read data 106 and generates the aligned read data 110. In some embodiments, the read data is aligned to a reference genome (although, one or more nucleotides within a read fragment may differ from the reference genome). In some instances, the DNA sequencer 104 may also align the read fragments and output aligned read data 110.

Aligned read data 110 may be any signal or data indicative of the read data 106 and the manner in which each fragment in the read data 106 is aligned. An example data format of the aligned read data 110 is the SAM format. A SAM file is a tab-delimited text file that includes sequence alignment data and associated metadata. Other data formats may also be used (e.g., pileup format).

Variant caller 112 may be any combination of hardware and software that detects variants in the aligned read data 110 and outputs potential variants 114. The variant caller 112 may identify nucleotide variations among multiple aligned reads at a particular location on a gene (e.g., a heterozygous SNP), identify nucleotide variations between one or more aligned reads at a particular location on a gene and a reference genome (e.g., a homozygous SNP), and/or detect any other type of variation within the aligned read data. The variant caller 112 may output data indicative of the detected variants in a variety of file formats, such as variant caller format (VCF) which specifies the location (e.g., chromosome and position) of the variant, the type of variant, and other metadata.

A variant caller 112 may evaluate the aligned read data 110 according to a particular level of sensitivity. In some instances, the variant caller 112 may perform a preliminary assessment of a particular variant to determine the "quality" of that variant. The sensitivity setting of a variant caller 112 may specify a minimum quality level to satisfy the detection of a variant. If the sensitivity setting is low, poor quality variants may be dismissed at this stage as likely false positives. On the other hand, if the sensitivity is high, even poor quality variants may be considered potential variants for subsequent analysis. High sensitivity settings are more likely to capture true variants, while also detecting false positive variant calls.

Potential variants 114 may be any combination of data that is indicative of the detected variants. In some implementations, the potential variants 114 include detected variants and their associated read pileups, along with any other information. The potential variants 114 may include both true positive variant calls (and associated read pileup data) along with false positive variant calls (and associated read pileup data).

B. Reference Genome

As described herein, a "reference genome" may refer to DNA sequencing data and/or an associated predetermined nucleotide sequence for a particular sample. A reference genome may also include information about the sample, such as its biopsy source, gender, species, phenotypic data, and other characterizations. A reference genome may also be referred to as a "gold standard" or "platinum" genome, indicating a high confidence of the accuracy of the determined nucleotide sequence. A reference genome and its associated read data may serve as a basis for training the background model as described in the present disclosure. An example reference genome is the NA12878 sample data and genome. See also Zook, J. M. et al. (2014) Nat. Biotechnol. Vol. 32 No. 3, 245-253.

C. DNA Read Data and Data Formats

DNA read data may be stored in a variety of file formats, such as FASTQ format files, SAM (Sequence Alignment/Map) files, BAM files (binary SAM files), VCF (Variant Call Format) files, and pileup files, among other possible file formats. Each of these file formats may store different information about the DNA read data at various stages within an analysis pipeline.

In some instances, an NGS sequencer may initially output read data in the FASTQ format, which includes nucleotide sequences and associated quality scores (e.g., Phred scores) in an ASCII format (or any other encoding). Then, by comparing the sequence data in the FASTQ file against a reference, a computing device may generate a SAM file that represents aligned read data. In some cases, the SAM file may be compressed and stored as a BAM file. SAM or BAM files may then be provided to a variant caller, which generates VCF files that contain aligned nucleotide sequences along with information about the detected variant. In some instances, the variant data may be stored in the pileup data format.

Each of the data formats may be stored as a text file, binary file, or in another format. For example, some embodiments of the present disclosure map variant data to pixel information (e.g., color, alpha, coordinates, etc.), such that a particular variant read pileup forms an image. Such a transformation from text or binary data to image data may be carried out in a lossless manner, such that the nucleotide bases, quality scores, reference, and other metadata of a read pileup can be extracted from the colors of the pixels and the arrangement of the pixels in the image. In some embodiments, an NGS analysis pipeline might carry out image processing on such image data.

C. DNA Variant Types and Detection

As described herein, a genome may contain multiple chromosomes, each of which may include genes. Each gene may exist at a position on a chromosome referred to as the "gene locus." Differences between genes (i.e., one or more variants at a particular gene locus) in different samples may be referred to as an allele. Collectively, a particular set of alleles in a sample may form the "genotype" of that sample.

Two genes that differ from each other (in terms of length, nucleotide bases, etc.) may include one or more variants. In some instances, a single sample may contain two different alleles at a particular gene locus; such variants may be referred to as "heterozygous" variants. Heterozygous variants may exist when a sample inherits one allele from one parent and a different allele from another parent; since diploid organisms (e.g., humans) inherit a copy of the same chromosome from each parent, variations likely exist between the two chromosomes. In other instances, a single sample may contain a gene that varies from a reference genome; such variants may be referred to as "homozygous" variants.

Many different types of variants may be present between two different alleles. Single nucleotide polymorphism (SNP) variants exist when two genes have different nucleotide bases at a particular location on the gene. Insertions or deletions (INDELs) exist between two genes when one gene contains a nucleotide sequence, while another gene contains a portion of that nucleotide sequence (with one or more nucleotide bases removed) and/or contains additional nucleotide bases (insertions). Structural differences can exist between two genes as well, such as duplications, inversions, and copy-number variations (CNVs).

Depending on the sensitivity and implementation of a variant caller, read data from a whole genome may include millions of potential variants. Some of these potential variants may be true variants (such as those described above), while others may be false positive detections. A deep learning model for variant calls may identify and weight features that distinguish true variants from false positives.

D. Machine Learning Tools

Machine learning generally refers to a computational technique in which a model is developed for classifying information. A machine learning tool may be trained using training data to classify information according to one or more variables (also referred to as "features"). A model may be trained using supervised learning or unsupervised learning. In supervised learning, a model is trained using labeled examples, where each example is paired with a label indicating the desired classification for that example. In unsupervised learning, a model is trained using unlabeled examples, and the model identifies features and/or classifications based on differences between those examples.

Generally, supervised learning is effective when features that distinguish between two or more classifications is well known. Consider a model that distinguishes between stop signs and yield signs. Features that distinguish between the two types of traffic signs include shape (octagon vs. triangle), color (red vs. yellow, in some cases), and text ("STOP" vs. "YIELD"). In this example, an accurate model can be trained on the basis of these handcrafted features, since the differences between the two types of traffic signs is well known.

However, the effectiveness of supervised learning can diminish when the number of features that distinguish between two classifications increases. For example, yield signs may be red, shaped like a rotated square, and might contain no text or text other than "YIELD" The classifier trained via supervised learning from the features described above might not accurately detect these yield signs that do not strictly adhere to the hand-selected features.

Thus, a classifier trained using supervised learning tends to perform well when the handcrafted features distinguishing two classifications are well understood. Although the classifier might detect a substantial number of yield signs correctly, some images of yield signs with features not considered during supervised training might be incorrectly classified or otherwise not considered to be yield signs.

Likewise, in the context of DNA sequencing and NGS variant detection, the robustness of a classifier trained to distinguish true positive variants calls from false positive variant calls is limited by the extent to which the features considered by the classifier cover all possible differences between true positives and false positives. Unlike traffic signs, the differences between true positive and false positive variant calls can be subtle and complex. A given variant call may include aligned read data in a pileup window (with each read containing a series of nucleotides), quality scores, a reference genome, and other information. Two variant calls can vary in millions of ways (i.e., "parameters"), and the extent to which each parameter impacts the classification between a true positive and a false positive may vary widely. Thus, hand-selecting the relevant features that distinguish true positive variant calls from false positive variant calls may result in an incomplete or inaccurate assessment of those variant calls, potentially leading to incorrect classifications (e.g., identifying false positives that are true variants, or identifying true variants that are false positives).

Furthermore, the features that distinguish true positives variant calls from false positive variant calls may be different for each DNA sequencing read process. Each DNA sequencing read process may involve different chemical processes, read lengths, machines, and alignment techniques. As such, the sources of error (which lead to false positive variant calls) of one read process may differ from those of another read process. Thus, a classifier that considers the same hand-selected features for multiple read processes may be inaccurate, to the extent that those read processes have different sources of error. It would not be feasible for a human to manually assess each read process and hand-select features for each of those read processes. Also, as NGS technologies continue to advance, changes to read processes could change the nature and source of errors.

Unsupervised learning, on the other hand, may be used to extract features from complex data sets. Whereas supervised learning involves training a classifier on the basis of handcrafted features, unsupervised learning involves the discovery of features that distinguish between two or more classifications. Unsupervised learning can be effective when features of a complex data set are not well known, allowing a machine learning tool to classify an example on the basis of complex patterns involving many features.

Some example deep learning tools and architectures include deep neural networks, convolutional neural networks (CNNs), and belief networks, among other possible architectures. These artificial neural networks may include multiple layers, each of which includes a collection of artificial neurons that may be interconnected in various ways. An example layer may include input nodes that correspond to different sources of input data (e.g., pixel values in an image). Another layer may include a set of interconnected nodes that carry out functions (e.g. rectifier functions, activation functions, etc.) that can provide linear or non-linear pooling to transform a large number of extracted features from the input layer into aggregated feature values. Yet another layer may be a fully-connected classification layer that weights each of the feature values from the pooling layer and outputs a probability value (e.g., a real number between 0 and 1). The specific configuration of each layer and the hyperparameters of the neural network may vary, depending upon the format and type of input data, the number of desired features, and the number of desired output classifications.

Once the features and patterns have been extracted from a data set, those features may serve as a basis for supervised training of other machine learning tools (e.g., classifiers). For a data set containing many variant calls, the unsupervised learning tool might characterize each variant call according to the extracted features. Then, by comparing those characterizations to known classifications of the variant calls, supervising learning can be carried out to generate a classifier.

The supervised training of a classifier may involve determining labels for each variant call of a reference genome. For example, a variant call at a specific position in a gene might contain two or more overlapping reads of different nucleotides, while the reference nucleotide at that position from the reference genome indicates that there is no heterozygous SNP; that variant call may be labeled as a "false positive," since a SNP was detected at a position in the reference genome known to contain only a single nucleotide. Conversely, if the reference genome species a SNP at that reference nucleotide position, the variant call may be labeled as a "true positive," since a known SNP was detected.

III. EXAMPLE ANALYSIS PIPELINE

A. Pipeline with False Positive Variant Filtering

NGS pipelines of the present disclosure may be similar to the pipeline 100 illustrated in FIG. 1, and also include one or more stages for evaluating the potential variants 114 to detect false positive variant calls. A trained deep learning model may receive the potential variants 114 (or data representative of the potential variants 114, the associated read pileup data, and/or any other metadata) and determine, for each potential variant, a likelihood (e.g., a real number between 0 and 1) that the potential variant is a false positive. The likelihoods, along with the potential variants and associated data, may be provided as an output to a computing device and/or provided as an input into another stage in an analysis pipeline.

B. Training the Model

Generating a classifier or model for determining likelihoods of variant calls being false positives involves a combination of unsupervised learning and supervised learning. Initially, training a deep learning network with variant calls from a reference genome produces a background model that has encoded therein features that distinguish those variant calls from each other. The reference genome may include labels for each variant call (e.g., whether the variant is a true positive or false positive). Using these labels, the classifications discovered by the deep learning network may be characterized via supervised learning.

Figure 2:
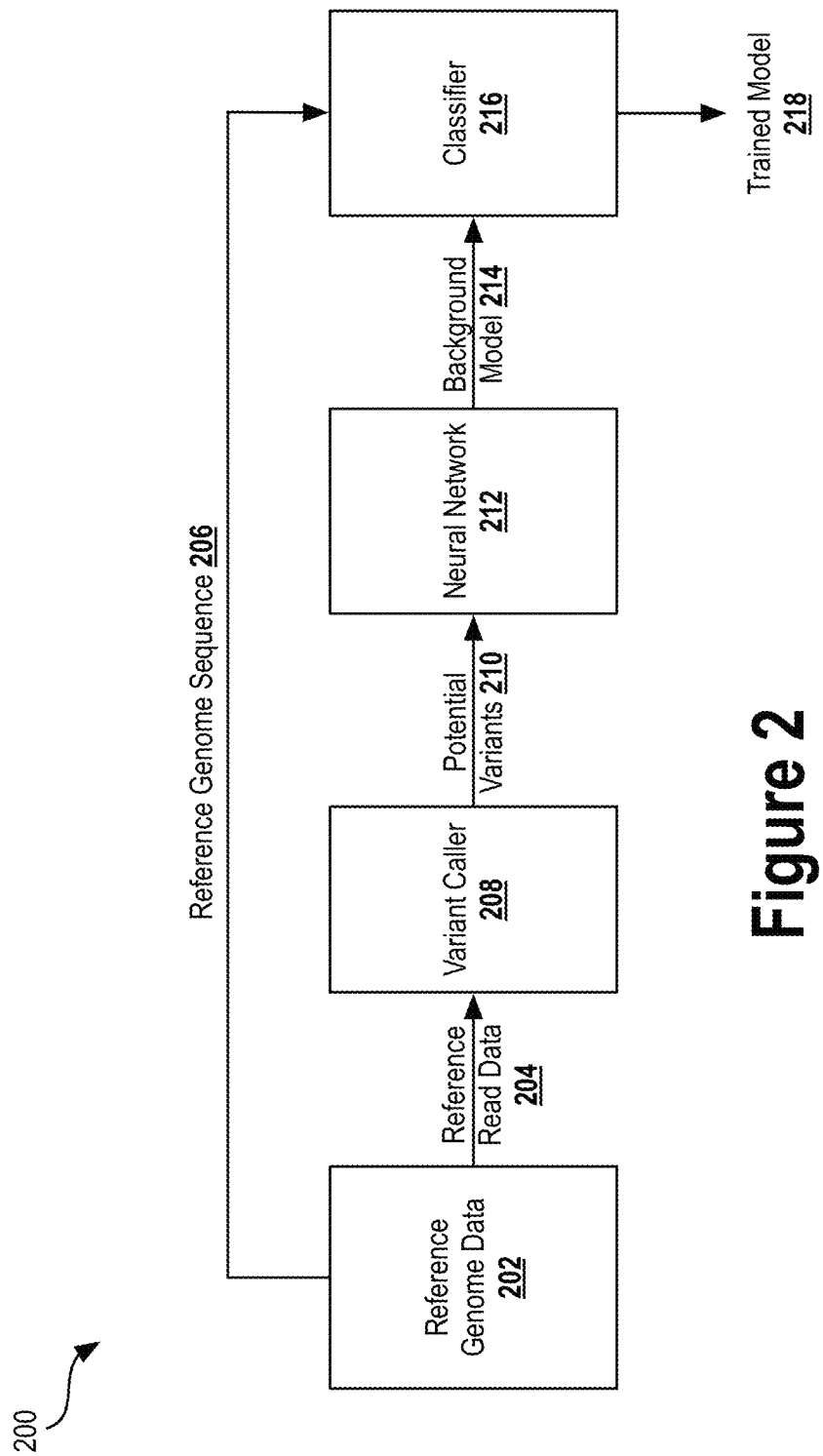
FIG. 2 illustrates a block diagram of a pipeline for generating a model, according to an example embodiment.

FIG. 2 illustrates a block diagram of a pipeline 200 for generating a trained model 218, according to an example embodiment. The pipeline 200 includes reference genome data 202, a variant caller 208, a neural network 212, and a classifier 216. The reference genome data 202 may include reference read data 204 and reference genome sequence 206. The variant caller 208 may receive the reference read data 204 as input and may generate potential variants 210. The neural network 212 may receive the potential variants 210 as training data, which produces a background model 214. The classifier 216 may use the background model 214 and the reference genome sequence 206 as a basis for producing a trained model 218.

The reference genome data 202 may include any combination of data that represents DNA read fragments, the alignment of those read fragments, a nucleotide sequence of the genome, and any other metadata for a particular sample.

As one example, a reference genome 202 may include data output from an NGS sequencer that sequenced a sample from an individual. In some instances, the reference genome data 202 may include read data generated using a single read process, such that subsequent stages in the pipeline characterize errors from that single read process. In other instances, the reference genome data 202 may include read data generated from multiple different read processes, such that multiple models may be produced corresponding to each read process.

The read data 204 may be similar to or the same as read data 106. In some embodiments, the reference read data 204 may be aligned, similar to or the same as aligned read data 110. The reference genome sequence 206 may be a nucleotide sequence of the whole reference genome. The variant caller 208 may be similar to or the same as the variant caller 112 described above. The potential variants 210 may be similar to or the same as the potential variants 114 described above.

The neural network 212 may be any deep learning network that receives potential variants 210 (or data representations of potential variants 210) as inputs and generates the background model 214. The potential variants 210 may serve as training data from which the neural network 212 forms connections between nodes, removes connections between nodes, and/or weights connections between nodes in the network. In some implementations, the neural network 212 may be a CNN with multiple layers. Regardless of the particular implementation, the neural network 212 may be any type of deep learning tool capable of extracting features from the potential variants 210.

The background model 214 may refer to a trained neural network (i.e., the state of the neural network 212 after completing unsupervised training using the potential variants 210). The background model 214 may determine one or more features that distinguish the potential variants 210 from each other. The number of features, and the depth of the deep learning classification encoded within the background model 214 may depend upon the configuration of the neural network and/or the hyperparameters of the network.

In some implementations, the neural network includes a number of layers, including an input layer, one or more "hidden" layers, and a classification layer. The input layer may sample a variant call (e.g., an image representation of a variant call read pileup window). Each hidden layer may be a pooling layer, a rectified linear unit (ReLU) layer, a fully connected layer, or a down-sampling layer. The classification layer may then weight each of the feature values determined in the hidden layers to generate a single output value (e.g., a real number between 0 and 1 indicating a likelihood that the variant call is a false positive).

Accordingly, the "background model" may refer to the portion of a trained neural network encompassing the input layer and hidden layer(s). The classification layer—although described herein as a separate machine learning tool—may be included within the neural network 212. Supervised training of a classifier may thus involve determining the weights for the connections in the classification layer; that is, the weights between each feature value and the output value on the neural network.

The classifier 216 may be a machine learning tool that determines the likelihood that a variant call is a false positive variant call. The classifier 216 may evaluate a variant call based on features discovered by the neural network 212 and encoded within the background model 214. The likelihood value output by classifier 216 may be any value indicating a confidence level that the variant call is a false positive (where a high confidence value represents a strong likelihood that the variant call is a false positive).

Training the classifier 216 may involve supervised learning based on the background model 214, the reference genome sequence 206, and the potential variants 210. In some instances, the background model 214 may provide the features upon which the classifier bases its classification of variant calls. Each potential variant 210 may be associated with a predetermined label (e.g., true positive or false positive). In instances where no labels are predetermined, the labels for each variant call may be determined based on the potential variants 210 compared to a reference genome. The classifier 216 may then process the potential variants 210, evaluate the feature values for those variants, and classify those features based on the labels associated with the potential variants.

In other embodiments, the classifier 216 may be a classification layer of a CNN. The neural network 212 may first determine the features that distinguish false positives from true positives. The variant call labels may then be used to train the weights of the classification layer. Once trained, the neural network 212 and classifier 216 can receive an unlabeled input variant call and determine the likelihood that the variant call is a false positive. The combination of the trained neural network 212 (the background model 214) and the trained classifier 216 collectively forms the trained model 218. The trained model 218 may then be used to determine false positive likelihoods for variant calls from read data other than the reference read data 204.

Data representative of a variant call may be a read pileup window that encompasses the potential variant. A "read pileup window" may refer to aligned read data spanning across a number of base pairs. As an example, if the potential variant is a SNP at a particular position in a gene, the read pileup window may include any DNA fragment read data (or portion of a DNA fragment read data) that aligns with a reference genome sequence within a range of positions before or after the SNP location (e.g., a window spanning 20 nucleotide positions in a gene including the detected SNP). In some implementations, the read pileup information at a potential variant site may be mapped to pixel colors and locations to form an image.

In some implementations, the training data used to train the neural network 212 and/or the classifier 216 includes read pileup windows (or images representing read pileup windows) for each nucleotide position in the entire genome. For a reference genome where each variant site is known, each read pileup window may be labeled as either a "variant" or a "reference" (i.e., non-variant). Training the neural network 212 may involve providing each of the read pileup windows—including both known variants and non-variants—to neural network 212. Then, the classifier 216 may be trained using the "variant" or "reference" labels for each of those read pileup windows.

Note that the trained model 218 is associated with a particular read process (specifically, the read process used to generate the reference genome data). Thus, the trained model 218 may be applied to variants from read data generated using that same read process. If a different read process is employed (e.g., a different NGS sequencer, a different fragment base pair length, different amplification method, etc.), the trained model 218 may not accurately evaluate the likelihoods of false positive variant calls.

The trained model 218 may be stored in a computer readable storage medium. If a new sample is sequenced using the same read process, an analysis pipeline may retrieve the trained model 218 and use it to evaluate the variant calls for that new sample.

C. Applying the Model to Determine Likelihoods of False Positive Variant Calls

Figure 3:
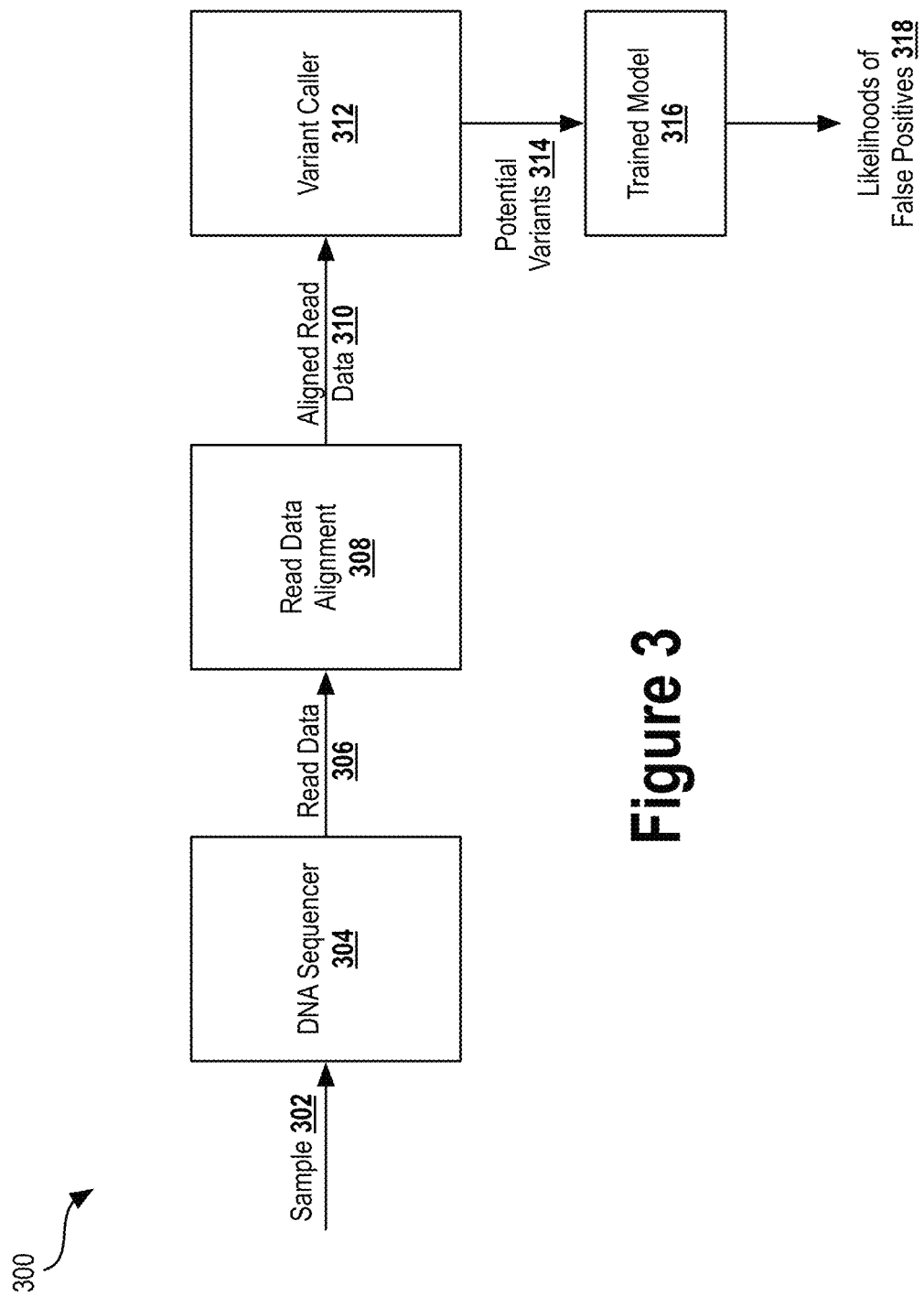
FIG. 3 illustrates a block diagram of a pipeline for evaluating variant calls using a model, according to an example embodiment.

FIG. 3 illustrates a block diagram of a pipeline 300 for evaluating variant calls using a model, according to an example embodiment. The pipeline 300 includes a sample 302, DNA sequencer 304, read data 306, aligned read data 310, variant caller 312, and potential variants 314, similar to the pipeline 100 illustrated in FIG. 1. In this example, the potential variants 314 are provided as inputs to the trained model 316. The trained model 316 may be a classifier trained using data from a reference genome sequenced using the same DNA sequencer as DNA sequencer 304. The trained model 316 may determine, for the potential variants 314, likelihoods 318 that the respective potential variants are false positive variant calls.

D. Different Models for Different Sequencing Methods

Figure 4:
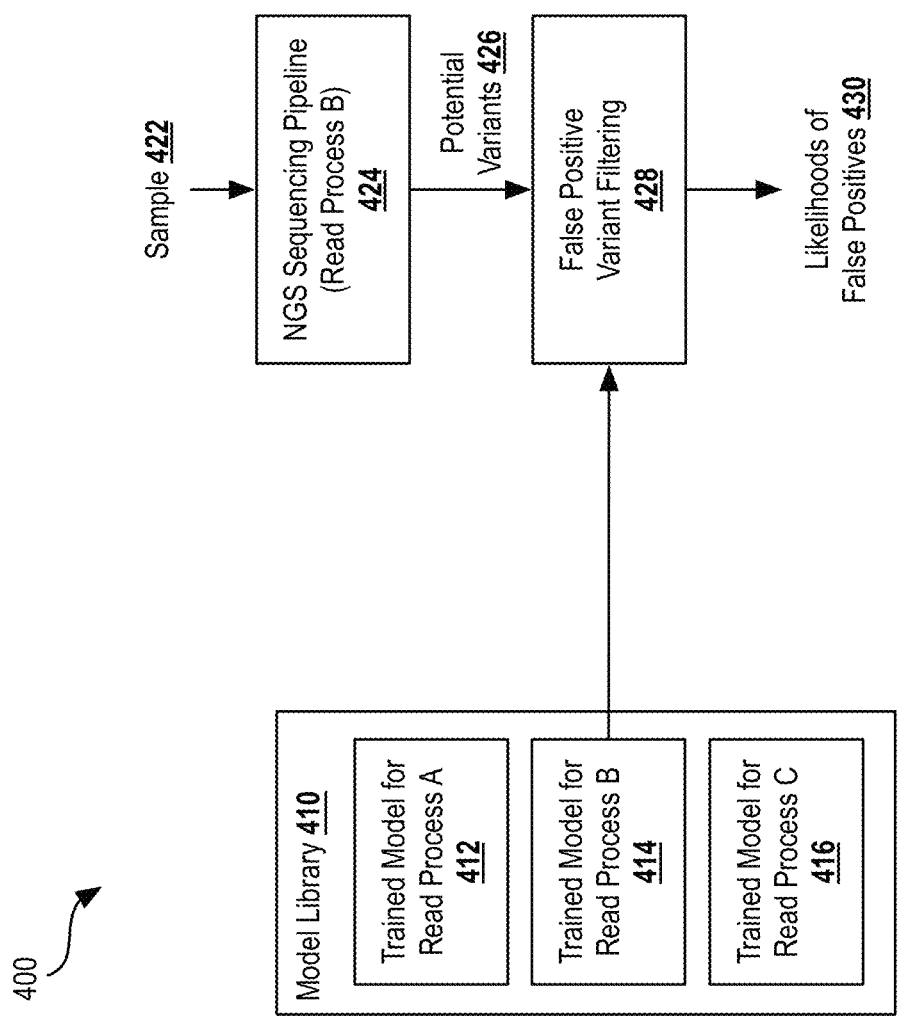
FIG. 4 illustrates a block diagram of a pipeline for evaluating variant calls using a model from a model library, according to an example embodiment.

FIG. 4 illustrates a block diagram of a pipeline 400 for evaluating variant calls using a model from a model library 410, according to an example embodiment. In this example, the model library 410 includes three models: trained model for read process A 412, trained model for read process B 414, and trained model for read process C 416. Each of these models were trained using reference genome data associated with the corresponding read process.

In an example set of operations, a sample 422 is provided as an input to an NGS sequencing pipeline 424, which uses read process B to perform the DNA sequencing. The NGS sequencing pipeline 424 may include an NGS sequencer, and may carry out read alignment and variant detection to generate potential variants 426. The potential variants 426 are then evaluated by the false positive variant filtering block 428.

The false positive variant filtering block 428 may receive the potential variants 426 and determine, based on metadata in the potential variants 426, for example, that the potential variants 426 are based on read data generated using read process B. The false positive variant filtering block 428 may then retrieve the trained model for read process B 414 from the model library 410. Using this model, the false positive variant filtering block 428 determines the likelihoods 430 that the potential variants 426 are false positive variant calls.

IV. EXAMPLE DEEP LEARNING NETWORKS

Figure 5:
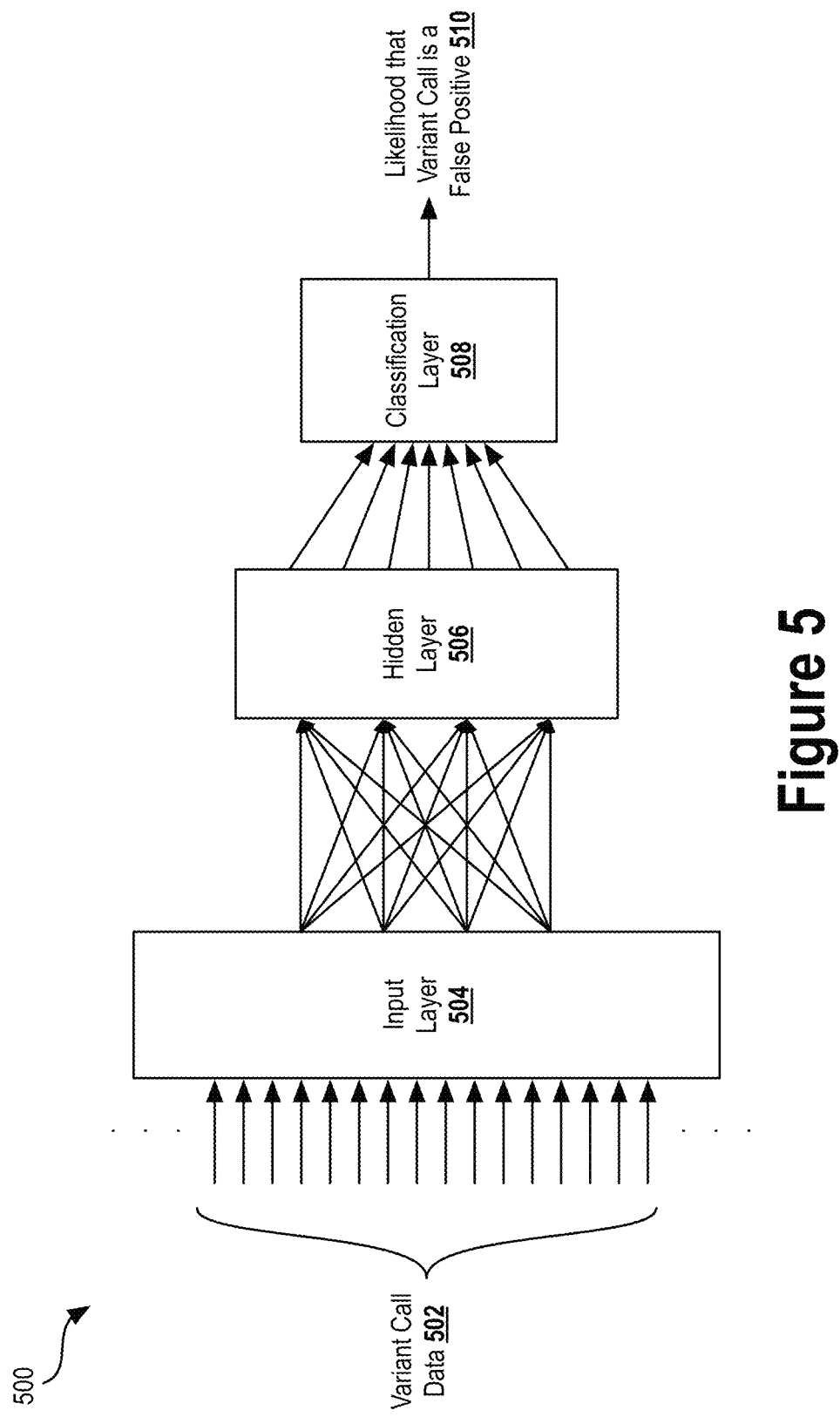
FIG. 5 illustrates a block diagram of a neural network, according to an example embodiment.

FIG. 5 illustrates a block diagram of a neural network 500, according to an example embodiment. The neural network includes an input layer 504, a hidden layer 506, and a classification layer 508. The input layer 504 receives variant call data 502 as input, which is decomposed and passed along to the hidden layer 506. Nodes of the hidden layer 506 may form connections with nodes in the classification layer 508. The classification layer 508 may then weight the feature value determinations from the hidden layer and map it to an output value representing the likelihood 510 that the variant call data 502 is a false positive variant call.

In some embodiments, the variant call data 502 may be an image representing a read pileup window that at least partially encompasses a potential variant. As one specific example, the image could be a 40×200 pixel image (representing a window that is 200 nucleotide positions wide and covering up to 40 different overlapping read fragments) with 3 color channels (e.g., red, green, and blue). Each pixel in the image may be mapped to information about a specific nucleotide at particular position aligned at a reference position with respect to a reference genome. One color channel might represent whether the nucleotide base is an A, C, G, or T. Another color channel might represent the "quality" score of that nucleotide read. Yet another color channel might be mapped to whether or not a read strand nucleotide exists at that location. Additionally, the transparency of the color channels with respect to a reference color (e.g., black) might indicate whether or not that pixel matches the reference genome (e.g., where fully transparent represents a mismatch, and fully opaque represents a match).

The variant call data 502 image may be provided to the input layer 504. More specifically, the pixels of variant call data 502 may be mapped input channels of the input layer 504.

The hidden layer 504 may include any combination of nodes and connections that collectively form a network. In some embodiments, the hidden layer 504 is a ReLU activation layer containing 15×15 nodes. The hidden layer may apply an elementwise activation function (e.g., a maximum function thresholding at zero).

The classification layer 506 may be a fully-connected layer that computes a score representing the likelihood that the input image represents a false positive variant read pileup window. In some embodiments, the classification layer 506 may be a logistic regression layer with 15×1 nodes and outputs a real number between 0 and 1.

In other implementations, additional layers may be included within the neural network 500. For example, the neural network 500 may include any number of convolutional layers, additional down-sampling or pooling layers, and/or other types of layers.

V. EXAMPLE MODEL OUTPUTS

Figure 6:
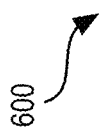
FIG. 6 is a table illustrating an output of a model, according to an example embodiment.

FIG. 6 is a table 600 illustrating an output of a model, according to an example embodiment. The table 600 may illustrate, for example, the output from the trained model 316, the output from false positive variant filtering block 428, and/or the output of neural network 500.

In an example analysis pipeline, a set of variant calls may be provided to a trained model to determine the likelihoods that those variant calls are false positives. Each variant call will have an associated "score" indicative of this likelihood. Table 600 illustrates this relationship between variant calls and likelihood scores. In this example, a likelihood of 1 indicates a 100% confidence level that the variant call is a false positive, whereas a likelihood of 0 indicates a 0% confidence level that the variant call is a false positive (in other words, a true positive). Note that, in other instances, the range of values that a score may take on may depend on the manner in which a trained classifier or classification layer is implemented.

In various embodiments, a subsequent analysis may be performed to determine whether or not each variant call is a false positive (i.e., a binary interpretation, rather than a confidence value). In some instances, a threshold level of confidence may be designated to indicate that the variant call is a false positive (e.g., likelihoods greater than 0.9 could be considered false positive, depending on the particular implementation). This threshold level of confidence may be selected manually, or might be determined on the basis of data. For instance, once the neural network and classifier are trained (i.e., both unsupervised and supervised learning has been completed), the training data may be provided to the classifier again to generate likelihood scores for each of the potential variants. Since the training data is labeled, each potential variant is known to be a true positive or a false positive. In some embodiments, the likelihood threshold might be set to the lowest likelihood output from the subset of the training data containing known false positives (i.e., the likelihood score associated with the known false positive example closest to the boundary between false positives and true positives).

The likelihoods may be output in a data format and/or provided to a computing device or storage medium. The likelihoods may also be graphically displayed to illustrate relationships between the likelihoods and one or more feature values, such as the feature values extracted from the neural network. The likelihoods may also be provided as inputs into subsequent analyses in which potential variants with high likelihood scores are discarded or otherwise labeled as false positives. In some contexts, such as personal genomics and clinical diagnoses, the likelihoods could be used to indicate a level of certainty that a particular patient has a certain trait or is afflicted with a particular genetic disease; this information could further provide a basis for evaluating medical treatment options or whether to perform certain diagnostic testing (e.g., if a certain variant is linked to a particular medical condition, a very low likelihood of the variant being a false positive might inform a doctor or patient to conduct further testing or diagnoses for verification).

Additionally, the variant call-likelihood pairs could serve as a basis for identifying sources of error in a particular NGS sequencer or analysis pipeline. If, for a particular read process, a specific variant call site is frequently associated with a high likelihood of being a false positive, then the false positive detection data could help pinpoint the source of error. By mining the variant call and likelihood data to identify sources of error, the accuracy and reliability NGS sequencers and analyses pipelines could be improved.

VI. EXAMPLE VARIANT CALL READ PILEUP WINDOWS

Figure 7A:
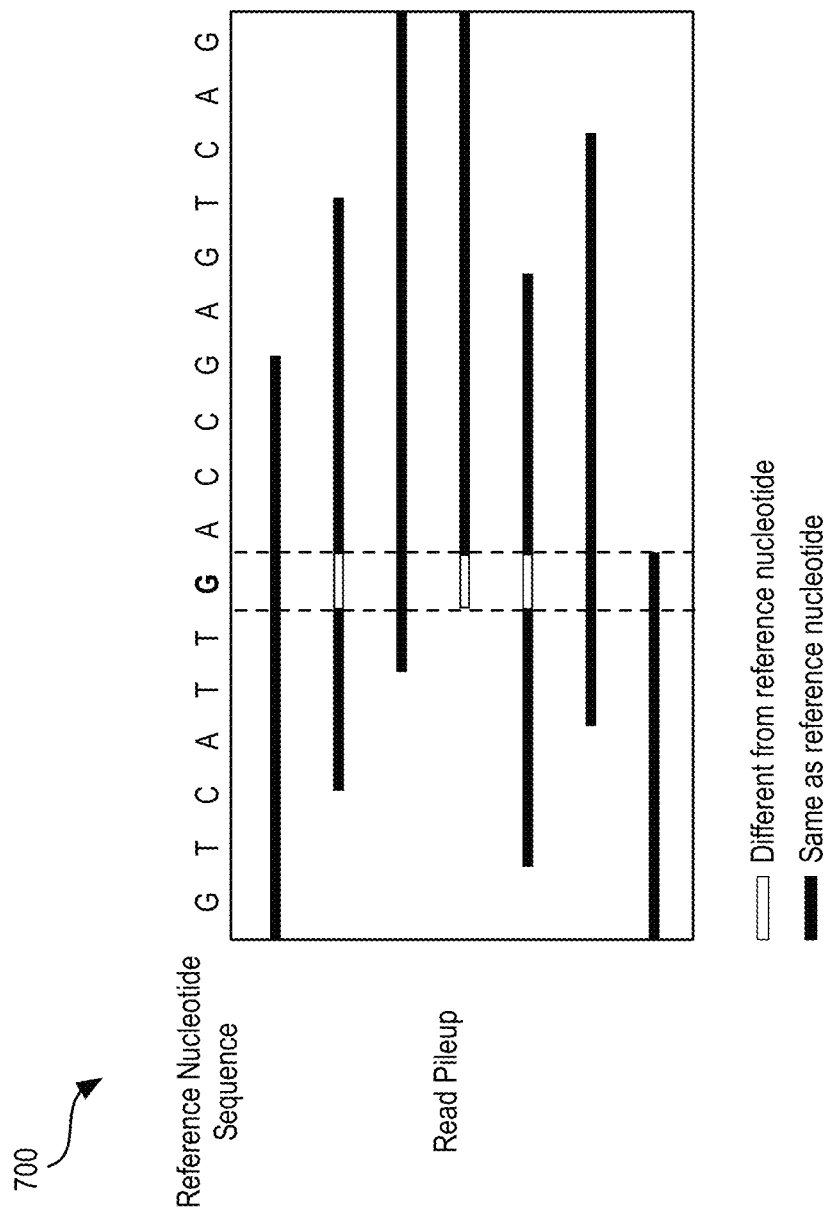
FIG. 7A illustrates a variant call read pileup window, according to an example embodiment.

FIG. 7A illustrates a variant call read pileup window 700, according to an example embodiment. In this example, the read pileup window includes seven read fragments that overlap at a particular nucleotide location (denoted by the dotted lines). The pileup window spans across seventeen nucleotide bases. In FIG. 7A, a read fragment that is colored black indicates that the nucleotide at that position is the same as the nucleotide in the associated reference nucleotide sequence (that is, the nucleotide base in the reference genome vertically aligned with that nucleotide). A read fragment that is colored white indicates that the nucleotide at that position is different from the nucleotide in the associated reference nucleotide sequence.

In this example, the second, fourth, and fifth read fragments (counting from the top down) have a different nucleotide than the associated nucleotide base in the reference genome. Depending on the variant caller, this read pileup window might be detected to be a SNP variant.

Figure 7B:
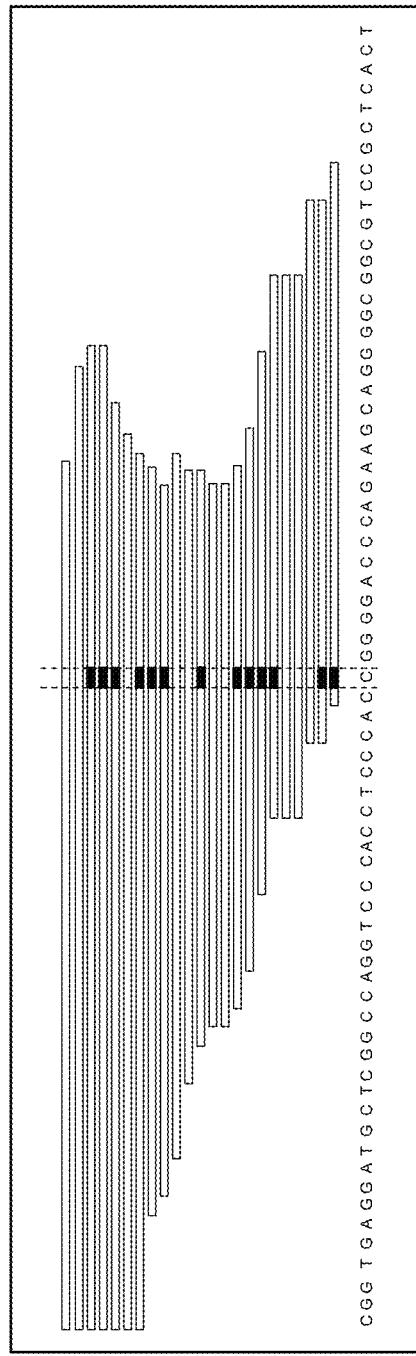
FIG. 7B illustrates a variant call read pileup window, according to an example embodiment.

FIG. 7B illustrates a variant call read pileup window 750, according to an example embodiment. The read pileup window 750 illustrated in FIG. 7B may be an example read pileup window similar to that depicted in FIG. 7A.

VII. EXAMPLE IMAGE REPRESENTATIONS OF VARIANT CALLS

Figure 8A:
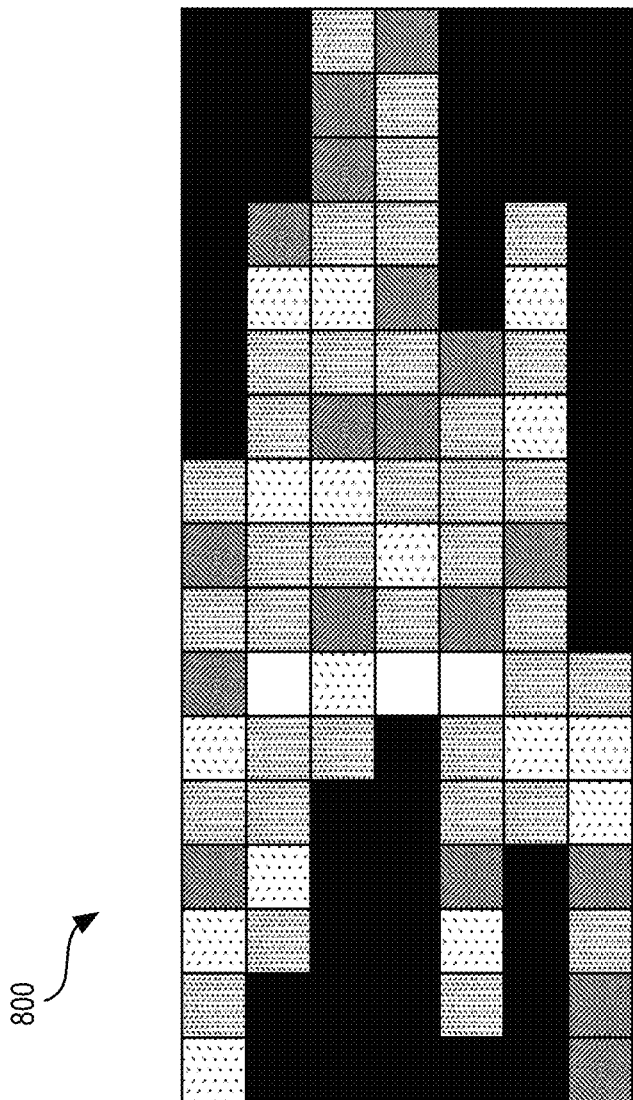
FIG. 8A illustrates an image representation of a variant call, according to an example embodiment.

FIG. 8A illustrates an image representation 800 of a variant call, according to an example embodiment. The image 800 in FIG. 8A represents the read pileup window 700 in FIG. 7A. Each pixel includes a horizontal position (a nucleotide position on the read fragment aligned with the reference genome) and a vertical position (the particular read fragment). In this example, black pixels indicate a lack of read fragment data at that position, while shaded pixels indicate the presence of a read fragment at that position. The extent of shading represents a combination of information (e.g., the nucleotide base, whether or not the base matches the reference genome, the quality score, etc.). If no shading is present in a pixel, the nucleotide base at that location differs from the nucleotide at that location in the reference genome.

Based on the shading (and, in other implementations, color), image analysis and pattern recognition performed by a neural network may identify patterns in the image. For example, the three non-shaded (white) squares in the image 800 represent a disagreement with the associated reference nucleotide. A neural network trained using a data set containing many example images (such as image 800) may detect features in the shading or color of the images that are indicative of false positives variants or true positive variants. Errors in the DNA sequencing process that lead to false positive detection may be graphically embodied in the images that represent read pileup windows; a neural network may be trained to identify these aberrations, colors, or other patterns in the images (generally, "features"). Once these graphical features have been identified, training a classifier or classification layer using labels for those images may generate a model capable to determining the likelihood of a read pileup window representing a false positive variant call based on characteristics and features of an image representation of that read pileup window.

Figure 8B:
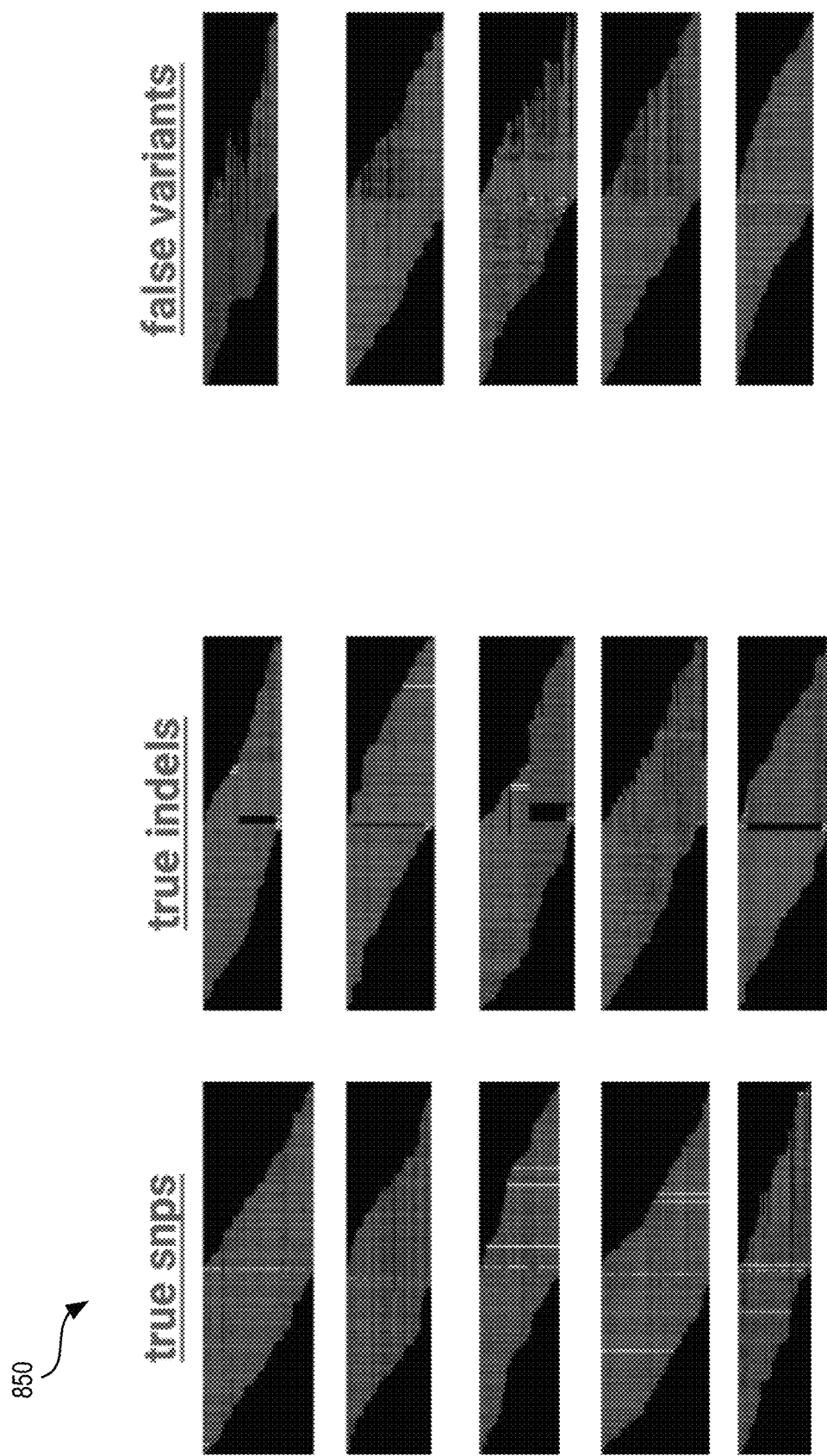
FIG. 8B illustrates image representations of variant calls, according to an example embodiment.

FIG. 8B illustrates example image representations 850 of variant calls, according to an example embodiment. In FIG. 8B, images labeled "true snps" represent read pileup windows that include SNPs, images labeled "true indels" represent read pileup windows that include insertions or deletions, and images labeled "false variants" represent read pileup windows of false positive variant calls. Note that FIG. 8B are example images similar to the image 800 depicted in FIG. 8A.

As shown in the image representations 850, the read pileup windows of true SNPs include distinct bright vertical lines. The read pileup windows of true INDELs include large dark gaps spanning large sections of the read pileup window. The read pileup windows of the false variants include small aberrations and inconsistent gaps (differences between the nucleotide base at that location and the associated reference nucleotide). These example image representations 850 illustrate that a neural network can detect such features as those described above in order to determine (or predict) the likelihood of that a non-labeled read pileup window is a false positive variant call.

VIII. PERFORMANCE COMPARISON BETWEEN DEEP LEARNING AND VQSR

Figure 9:
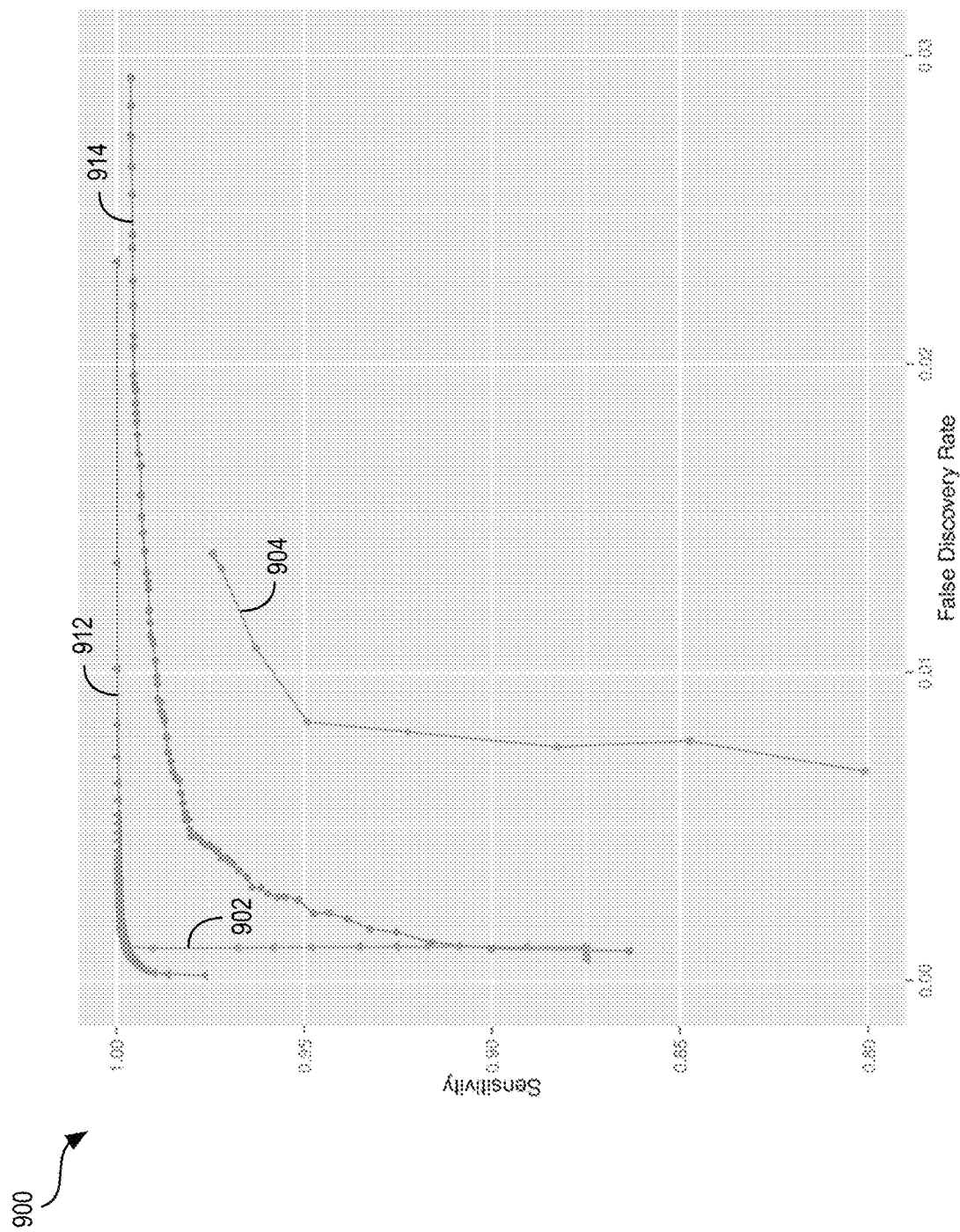
FIG. 9 illustrates a graph comparing the performance of a deep learning model and a classifier trained on handcrafted features, according to an example embodiment.

FIG. 9 illustrates a graph 900 comparing the performance of a deep learning model and a classifier trained on handcrafted features, according to an example embodiment. In this example, the classifier trained on handcrafted features is the Variant Quality Score Recalibration (VQSR), a tool of the Genome Analysis Toolkit (GATK) that evaluates the likelihood of a read pileup window being a false positive variant call on the basis of handcrafted features. The deep learning model is a convolution neural network, trained in a manner as described above which evaluates the likelihood of a read pileup window being a false positive variant call on the basis of features extracted from by the neural network from training data.

In graph 900, the horizontal axis is the false positive discovery rate; the larger the discovery rate, the greater number of false positives that are detected. The vertical axis is the sensitivity setting of the variant caller, where a larger number indicates a higher level of sensitivity (i.e., more true variants and more false variants detected).

In graph 900, the VQSR performance for SNP false positive discovery rate is illustrated by line 902 and the deep learning model's performance for SNP false positive discovery rate is illustrated by line 912. As illustrated in the graph 900, the VQSR false discovery rate does not increase significantly as the sensitivity increases; however, false discovery rate of the deep learning model increases as the sensitivity increases. Thus, the deep learning model outperforms VQSR for SNP false positive discovery.

Likewise, the VQSR performance for INDEL false positive discovery rate is illustrated by line 904 and the deep learning model's performance for INDEL false positive discovery rate is illustrated by line 914. As illustrated in the graph 900, the VQSR performance is good for lower sensitivities, but does not increase significantly as the sensitivity increases. In comparison, the false positive discovery rate of the deep learning model continues to increase beyond that of VQSR as sensitivity increases. Thus, the deep learning model outperforms VQSR for INDEL false positive discovery.

IX. EXAMPLE METHODS

Figure 10:
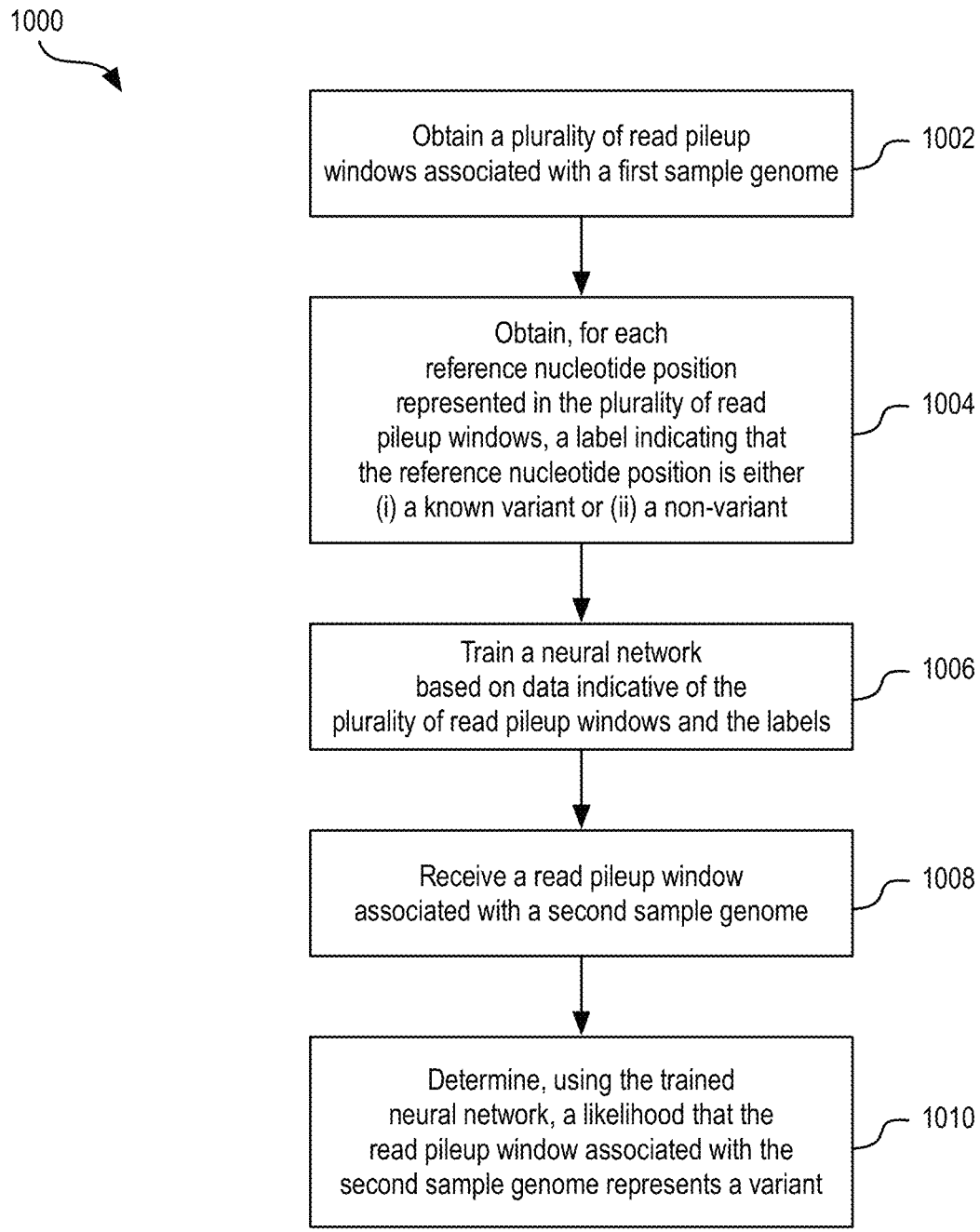
FIG. 10 is a flowchart of example operations for determining a flow path.

FIG. 10 is a flowchart of operations 1000 for determining a step path, according to an example implementation. Operations 1000 may include one or more actions as illustrated by blocks 1002-1010. Although the blocks are illustrated in sequential order, these blocks may also be performed in parallel, and/or in a different order than those described herein. Also, the various blocks may be combined into fewer blocks, divided into additional blocks, and/or removed based upon the directed implementation.

In addition, the operations 1000 and other operations disclosed herein show functionality of one possible implementation. In this regard, each block may represent a module, a segment, or a portion of program code, which includes one or more instructions executable by a processor or computing device for implementing specific logical operations or steps. The program code may be stored on any type of computer-readable medium, for example, such as a storage device included in a disk or hard drive. The computer-readable medium may include a non-transitory computer-readable medium, for example, such as computer-readable media that stores data for short periods of time like register memory, processor cache and/or random access memory (RAM). The computer-readable medium may also include non-transitory media, such as secondary or persistent long-term storage, like read-only memory (ROM), optical or magnetic disks, and compact-disc read-only memory (CD-ROM), for example. The computer-readable media may be considered a computer-readable storage medium, for example, or a tangible storage device.

In addition, one of more blocks in FIG. 10 may represent circuitry that is wired to perform the specific logical operations.

A. Obtain a Plurality of Read Pileup Windows Associated with a First Sample Genome Block 1002 involves obtaining a plurality of read pileup windows associated with a first sample genome. Each read pileup window includes a plurality of sequence reads that each include a nucleotide aligned at a reference nucleotide position within the first sample genome. The read pileup windows may be text or graphical representations of aligned read data spanning across a range of nucleotide positions in the first sample genome. Example depictions of read pileup windows are shown in FIGS. 7A and 7B.

Each sequence read within a read pileup window may contain metadata indicating the manner in which the first sample was sequenced (i.e., which read process was used), parameters of that read process, quality scores for each base pair, and any other information. The first sample genome may be data associated with a reference genome (e.g., NA12878, among other reference genomes).

B. Obtain Labels Indicating that the Reference Nucleotide Position is Either (i) a Known Variant or (ii) a Non-Variant Block 1004 involves obtaining, for each reference nucleotide position represented in the plurality of read pileup windows, a label indicating that the reference nucleotide position is either (i) a known variant or (ii) a non-variant. Data associated with the first sample genome may include a reference nucleotide sequence for the entire genome of the first sample. Each position in the nucleotide sequence may be associated with a known nucleotide base, or may be a location known to have a variant. Labels may indicate, for each nucleotide position in the entire genome, whether that position is associated with a variant, or is a single reference nucleotide (e.g., G, A, T, or C).

C. Train a Neural Network

Block 1006 involves training a neural network based on data indicative of the plurality of read pileup windows and the labels. The neural network may be a convolutional neural network, as described above. Training the neural network may involve a combination of unsupervised training and supervised training.

In some implementations, the operations 1000 include a step for generating a plurality of images that represent the plurality of read pileup windows. Each nucleotide position may be converted into pixel data which is mapped to an image. Training the neural network may involve using unsupervised learning to detect patterns or features in the images representative of the read pileup windows. Then, using the labels, a classification layer (or separate classifier) may be trained using supervised learning to classify those patterns and features as either representing true variants or false positive variant calls.

D. Receive a Read Pileup Window Associated with a Second Sample Genome

Block 1008 involves receiving a read pileup window associated with a second sample genome. The second sample genome may be a sample genome from a different organism than the first sample genome, which was sequenced using the same read process as the first sample genome. The read pileup window may include a potential variant detected by a variant caller.

E. Determine a Likelihood that the Read Pileup Window Associated with the Second Sample Genome Represents a Variant Block 1010 involves determining, using the trained neural network, a likelihood that the read pileup window associated with the second sample genome represents a variant. In some implementations, the likelihood may indicate a confidence level that the read pileup window represents a false positive variant call (i.e., is not a variant).

In addition to the blocks 1002-1010, the operations 1000 may also include steps for storing and/or outputting the determined likelihoods. In some instances, the likelihoods may be stored in a database or table on a storage medium. In other instances, the likelihoods may be output to computing systems or other analysis pipelines to serve as a basis for genotyping the second sample genome, conducting medical diagnoses, or otherwise be used in a study involving genomes from multiple organisms. In some embodiments, the likelihoods may be processed to identify sources of error in the read process used to generate the sequence reads in the read pileup windows.

X. CONCLUSION

It should be understood that arrangements described herein are for purposes of example only. As such, those skilled in the art will appreciate that other arrangements and other elements (e.g. machines, interfaces, operations, orders, and groupings of operations, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and implementations have been disclosed herein, other aspects and implementations will be apparent to those skilled in the art. The various aspects and implementations disclosed herein are for purposes of illustration and are not intended to be limiting, with the true scope being indicated by the following claims, along with the full scope of equivalents to which such claims are entitled. It is also to be understood that the terminology used herein is for the purpose of describing particular implementations only, and is not intended to be limiting.

What is claimed is:

1. A method comprising:
obtaining a plurality of read pileup windows associated with a first sample genome, wherein each read pileup window is associated with a respective different reference nucleotide position within the first sample genome, wherein each read pileup window includes sequence reads generated using a particular read process, and wherein a given read pileup window of the plurality of read pileup windows includes a plurality of sequence reads that each include a nucleotide aligned at the reference nucleotide position, within the first sample genome, that is associated with the given read pileup window;
obtaining, for each reference nucleotide position that is associated with a read pileup window within the plurality of read pileup windows, a label indicating that the reference nucleotide position is either (i) a known variant or (ii) a non-variant;
training a neural network, based on data indicative of the plurality of read pileup windows and the labels, to predict a likelihood that an input read pileup window represents a variant at a reference nucleotide location that is associated with the input read pileup window;
receiving a read pileup window that is associated with a second sample genome and that includes sequence reads generated using the particular read process; and determining, using the trained neural network, a likelihood that the read pileup window associated with the second sample genome represents a variant.

2. The method of claim 1, further comprising:
providing the likelihood as an output signal to a computing device.

3. The method of claim 1, wherein training the neural network comprises: performing unsupervised learning on the neural network to generate a background model; and based on the plurality of labels, the plurality of read pileup windows, and the background model, performing supervised learning on the neural network to generate the trained neural network.

4. The method of claim 1, wherein the neural network is a convolutional neural network.

5. The method of claim 1, wherein the neural network comprises an input layer, a hidden layer, and an output layer.

6. The method of claim 5, wherein the hidden layer is a rectified linear unit layer.

7. The method of claim 5, wherein the output layer is a classification layer that outputs a likelihood that a read pileup window represents a variant.

8. The method of claim 1,
wherein the data indicative of the plurality of read pileup windows includes a plurality of images representative of the plurality of read pileup windows,
wherein the method further comprises generating the plurality of images representative of the plurality of read pileup windows, and
wherein training the neural network comprises training the neural network based on the plurality of images representative of the plurality of read pileup windows.

9. The method of claim 8, wherein a given image representative of a given read pileup window includes a plurality of pixels corresponding to nucleotide positions on sequence reads, and wherein each pixel includes one or more color values that represent information about the sequence reads.

10. The method of claim 1, wherein the first sample genome is a reference genome.

11. The method of claim 1, further comprising:
determining that the read pileup window associated with the second sample genome represents a variant based on the likelihood being below a threshold value.

12. The method of claim 1, further comprising:
determining that the read pileup window associated with the second sample genome represents a variant based on the likelihood being above a threshold value.

13. A non-transitory computer-readable medium having instructions stored thereon that, upon execution by at least one processor, causes performance of operations comprising:
obtaining a plurality of read pileup windows associated with a first sample genome, wherein each read pileup window is associated with a respective different reference nucleotide position within the first sample genome, wherein each read pileup window includes sequence reads generated using a particular read process, and wherein a given read pileup window of the plurality of read pileup windows includes a plurality of sequence reads that each include a nucleotide aligned at the reference nucleotide position, within the first sample genome, that is associated with the given read pileup window;
obtaining, for each reference nucleotide position that is associated with a read pileup window within the plurality of read pileup windows, a label indicating that the reference nucleotide position is either (i) a known variant or (ii) a non-variant;
training a neural network, based on data indicative of the plurality of read pileup windows and the labels, to predict a likelihood that an input read pileup window represents a variant at a reference nucleotide location that is associated with the input read pileup window;
receiving a read pileup window that is associated with a second sample genome and that includes sequence reads generated using the particular read process; and
determining, using the trained neural network, a likelihood that the read pileup window associated with the second sample genome represents a variant.

14. The non-transitory computer-readable medium of claim 13, wherein the operations further comprise:
providing the likelihood as an output signal to a computing device.

15. The non-transitory computer-readable medium of claim 13, wherein the first sample genome is a reference genome.

16. The non-transitory computer-readable medium of claim 13, wherein the neural network is a convolutional neural network.

17. The non-transitory computer-readable medium of claim 13,
wherein the data indicative of the plurality of read pileup windows includes a plurality of images representative of the plurality of read pileup windows,
wherein the operations further comprise generating the plurality of images representative of the plurality of read pileup windows, and
wherein training the neural network comprises training the neural network based on the plurality of images representative of the plurality of read pileup windows.

18. The non-transitory computer-readable medium of claim 17, wherein a given image representative of a given read pileup window includes a plurality of pixels corresponding to nucleotide positions on sequence reads, and wherein each pixel includes one or more color values that represent information about the sequence reads.

19. A method comprising:
receiving a read pileup window associated with a second sample genome, wherein the read pileup window includes sequence reads generated using a particular read process;
obtaining, from a model library, a trained model associated with the particular read process, wherein the model library includes a plurality of trained models associated with a respective plurality of read processes, wherein each read process of the plurality of read processes represents a respective different method that includes generating a read pileup window by sequencing a sample of DNA;
determining, using the trained model, a likelihood that the read pileup window associated with the second sample genome represents a variant; and
providing the likelihood as an output signal to a computing device.

20. The method of claim 19, wherein the trained model is a convolutional neural network.

* * * * *